United States Patent
Dambinova (10) Patent No.: US 8,084,225 B2
(45) Date of Patent: Dec. 27, 2011

(54) METHODS FOR DIAGNOSING CEREBROVASCULAR EVENTS BASED ON NR2 PEPTIDES

(75) Inventor: Svetlana A. Dambinova, Atlanta, GA (US)

(73) Assignee: CIS Biotech, Inc., Atlanta, GA (US)

( * ) Notice: Subject to any disclaimer, the term of this patent is extended or adjusted under 35 U.S.C. 154(b) by 501 days.

(21) Appl. No.: 11/916,507

(22) PCT Filed: Jun. 13, 2006

(86) PCT No.: PCT/US2006/023020
§ 371 (c)(1), (2), (4) Date: Sep. 16, 2008

(87) PCT Pub. No.: WO2006/135893
PCT Pub. Date: Dec. 21, 2006

(65) Prior Publication Data
US 2009/0181006 A1 Jul. 16, 2009

Related U.S. Application Data

(60) Provisional application No. 60/689,806, filed on Jun. 13, 2005.

(51) Int. Cl.
*G01N 33/00* (2006.01)
*G01N 33/48* (2006.01)
*G01N 33/50* (2006.01)

(52) U.S. Cl. ......... 435/7.95; 435/7.21; 530/412; 702/19

(58) Field of Classification Search ................... None
See application file for complete search history.

(56) References Cited

U.S. PATENT DOCUMENTS

2003/0096331 A1 * 5/2003 Dambinova ............... 435/7.92

OTHER PUBLICATIONS

Dambinova and Skoromets, Stroke, 33: 1181-1182, 2002.*
Lai et al. Stroke, 25(5):958-962, May 1994.*

* cited by examiner

*Primary Examiner* — Lorraine Spector
*Assistant Examiner* — Stacey MacFarlane
(74) *Attorney, Agent, or Firm* — Arnall Golden Gregory; Clark G. Sullivan; Qian Zhang (57) ABSTRACT

Methods and kits for diagnosing and treating cerebrovascular events, and for defining the time and anatomical location of an event, are provided based on the detection and quantification of bound or total and unbound NR2 peptides in biological fluids. The methods are optionally performed in conjunction with neurological scoring and neuroimaging, and are directed to risk assessment, prognosis, diagnosis and treatment of TIA and stroke on an emergency basis in the emergency room.

5 Claims, 4 Drawing Sheets

Fig. 1. Distribution of unbound NR2 peptide in plasma of studied patients (n=40)

Fig. 2. The distribution of bound NR2 peptide in serum of studied patients (n=40)

Fig. 3.

Stroke severity assessment by NIH Stroke Scale

| Item | Response | Item | Response |
|---|---|---|---|
| 1a. Level of consciousness | 0= Alert<br>1= Not alert<br>2=Obtunded<br>3= Unresponsive | 6. Motor leg<br>  a. Left<br>  b. Right | 0 = No drift<br>1 = Drift before 5 s<br>2 = Falls before 5 s<br>3 = No effort against gravity<br>4 = No movement |
| 1b. Level of consciousness questions | 0 = Answers both correctly<br>0 = Answers one correctly<br>1 = Answers neither correctly | 7. Ataxia | 0= Absent<br>1= One limb<br>2 = Two limbs |
| 1c. Level of consciousness | 0 = Performs both tasks correctly<br>1 = Performs one task correctly<br>2 = Performs neither task | 8. Sensory | 0= Normal<br>1= Mild loss<br>2 = Severe loss |
| 2. Gaze | 0= Normal<br>1= Partial gaze palsy<br>2= Total gaze palsy | 9. Language | 0= Normal<br>1= Mild aphasia<br>2= Severe aphasia<br>3 = Mute or global aphasia |
| 3. Visual fields | 0 = No visual loss<br>1 = Partial hemianopsia<br>2 = Complete hemianopsia<br>3 = Bilateral hemianopsia | 10. Dysarthria | 0 = Normal<br>1 = Mild<br>2 = Severe |
| 4. Facial palsy | 0 = Normal<br>1 = Minor paralysis<br>2 = Partial paralysis<br>3 = Complete paralysis | 11.Extinction/ inattention | 0 = Normal<br>0 = Mild<br>2 = Severe |
| 5. Motor aim<br>  a. Left<br>  b. Right | 0 = No drift<br>1 = Drift before 5 s<br>2 = Falls before 10 s<br>3= No effort against gravity<br>4 = No movement | | |

The detailed instructions for the use of the scale are available at: http://www.ninds.nih.gov/doctors/NIH_Stroke_Scale.pdf. An online course for provider education is available at: http://asa.trainingcampus.net/uas/modules/trees/index.aspx.

Fig. 4.

METHODS FOR DIAGNOSING CEREBROVASCULAR EVENTS BASED ON NR2 PEPTIDES

RELATION TO PRIOR APPLICATIONS

This application claims priority 35 U.S.C. §119(e) to U.S. Provisional Application No. 60/689,806, filed Jun. 13, 2005.

FIELD OF THE INVENTION

The invention relates to methods and kits for diagnosing and treating cerebrovascular events, and for defining the time and anatomical location of an event, based on the detection and quantification of bound or total and unbound NR2 peptides in biological fluids. The methods are optionally performed in conjunction with neurological scoring and neuroimaging, and directed to risk assessment, prognosis, diagnosis and treatment of TIA and stroke on an emergency basis in the emergency room and in a primary care setting.

BACKGROUND OF THE INVENTION

Cerebrovascular Accident and Transient Ischemic Attack

Transient ischemic attack portends significant future risk of stroke and its associated morbidity and mortality. Patients with transient ischemic attack require further evaluation to assess for any potentially reversible underlying disease process. Despite the significant impact of this disease process there is still no definitive guidance concerning the early evaluation and disposition of such patients presenting to the Emergency Department. The Stroke Council of the American Heart Association states there is no prospective data concerning the justification for inpatient evaluation of patients with TIA. They conclude that "the decision whether to hospitalize a patient depends on that patients individual circumstances." Considerable regional practice variation exists in the initial evaluation of such patients on an inpatient versus outpatient basis. The rationale for inpatient care is to expeditiously obtain diagnostic studies, evaluate risks for future events, monitor the patient for recurrence or worsening symptoms, and to institute any needed interventions including operative therapy. Current recommendations for the evaluation and treatment of patients with TIA are well described. The guidelines suggest a battery of laboratory tests and radiologic studies along with recommendations concerning medical and surgical therapy.

It appears that a certain subset of patients presenting to the Emergency Department with symptoms suggestive of TIA are at substantial risk in the short term of suffering a completed stroke. In a recent Emergency Department-based observational cohort study involving 1707 patients presenting with symptoms suggestive of TIA, 10.5% of patients developed stroke within 90 days. Significantly, half of those patients developed a stroke within the first 2 days. Johnston et al retrospectively identified five independent risk factors for stroke within 90 days (age>60, Diabetes, Duration of symptoms >10 min., Weakness, Speech impairment). By combining the independent risk factors, subgroups were identified with minimal (0%) to high (34%) short-term risk of stroke.

Such high-risk patients are unlikely to receive a complete diagnostic evaluation and implementation of an appropriate therapeutic regimen (medical or surgical) as an outpatient in less than 48 hours. Further complicating the decision process is the degree of diagnostic certainty in patients with a suspected TIA. Transient ischemic attack is a clinical diagnosis and inter-observer reliability concerning the diagnosis is often poor. Therefore, in the setting of current practice patterns in many institutions, some patients without true neurologic disease are admitted as well as others who may fare just as well with an outpatient evaluation. Prospective validation of a set of risk factors identifying patients who complete stroke within days of a sentinel TIA would allow for the derivation of a clinical prediction rule. This would allow for identification of patients at high risk in the near term that require admission as well as those who may be safely discharged for an outpatient evaluation. Such "stratification of stroke risk" would allow targeting of more aggressive interventions to those at greatest short-term risk.

Current Alternatives to Stroke Diagnosis

The medical community has several technologies to diagnose stroke. Although numerous, none of these technologies is able to predict stroke or directly diagnose cerebrovascular abnormalities or TIA/stroke. In the stroke treatment field, the adage all physicians live by are "Time is Brain".

The National Institute of Neurological Disorders and Stroke (NINDS) recommends the following time guidelines for managing ischemic stroke:

| | |
|---|---|
| Door to physician | 10 min |
| Door to neurologic consultation | 15 min |
| Door to CT completion/interpretation | 45 min |
| Door to thrombolytic treatment | 60 min |
| Door to neurosurgical consultation | 2 hr |

Emergency Departments at major hospitals have a wide range of options for diagnosing stroke. More than 90% of hospitals with more than 200 beds have access to CT scanners, enabling them to quickly (<15 min) evaluate a potential stroke patient to rule out hemorrhagic stroke and stroke mimics. It is theoretically possible for CT to positively identify 100% of parenchymal and 85 to 97% of subarachnoid hemorrhages, however overall accuracy of recognition of ischemic vs. hemorrhagic falls with interpretation to between 67 and 83 percent.

A large percentage of hospitals now have Magnetic Resonance Imaging (MRI) capability. However, MRI scans require a longer time window for imaging. Currently MRI does not readily distinguish hemorrhagic stroke prior to 6 hrs and is thus not considered a primary diagnostic modality. A relatively new technology, Diffusion-Weighted Magnetic Resonance Imaging (DWI) can rapidly detect perfusion decreases in patients with high risk of TIA. Initial data found DWI predictive within less than 10 minutes of ischemic change. Scanning sequences can be obtained in 30 to 60 seconds of scanner time. Although effective, each of these imaging techniques is limited by high capital costs and service requirements. Furthermore, they require specially trained technicians to operate and interpret the results.

Other technologies, including Doppler Ultrasound, Single-Photon Emission Computerized Tomography, Xenon-Computerized Tomography, CT Angiography, and MR Perfusion Imaging have been omitted either for lack of a global diagnostic approach or the early stage of the current technology.

There are no blood tests currently available in the Emergency Department that answer these unmet diagnostic needs by diagnosing acute cerebrovascular accidents, TIA, and ischemic stroke and ruling out stroke mimics.

Brain NR2 Peptide and Antibody as Biomarkers of TIA/stroke

The majority of studies involving markers of the central nervous system come from brain injury or cardiothoracic literature. However the most significant marker for brain ischemia is NMDA receptors that are involved in the neurotoxicity cascade underlying cerebral ischemia.

Excitatory amino acids (EAAs) play an important role during stroke. Cerebral ischemia induces glutamate release, and activates EAA receptors. Blocking glutamate release or its interaction with EAA receptors has been reported to reduces cerebral damage. N-methyl-D-aspartate receptors (NMDAR), a member of the ligand-gated ion EAA channel complex, contain NR1, NR2 and NR3 subunits. Of these subunits, NR2 has been reported to be involved in several neurological disorders, including ischemia and hypoxia. The NR2 subunit consists of 4 different subtypes, NR2A-2D, which are encoded by different genes. Both NR2A and NR2B are found in the cerebral cortex and hippocampus whereas NR1 is ubiquitous to all NMDAR complexes located in brain and peripheral organs.

Over-stimulation of glutamate receptors during ischemia induces excessive $Ca^{2+}$ influx and activation of thrombin-activated serine proteases, which facilitates the cleavage of external N-terminal domain of NMDAR on cell membranes. The N-terminal peptide fragments of NMDAR, translocated to the bloodstream through the damaged blood-brain barrier, can possibly act as "foreign" antigens and initiate an immune response that generates antibodies in the blood. However the interaction between time course of NR2 peptide/antibodies in blood and NR2 mRNA expression in brain remains unclear.

Recently, NMDAR peptides and their antibodies have been proposed for the treatment of stroke and epilepsy (During et al, Science, 2000, 287:1453-60) and as biomarkers of neurotoxicity underlying cerebral ischemia and stroke (Dambinova S A, et al. Stroke 2002; 33:1181-1182; Dambinova S A, et al. Clin Chem 2003; 49:1752-1762). With neuronal death or ischemia, NR2 peptide fragments of the NMDA receptor break off and appear in the bloodstream and generate an antibody response. Dambinova et al. have reported that the peptide fragments and antibodies can both be detected in blood samples (Dambinova SA, et al. Stroke 2002). They have further reported that adult patients who have suffered an acute ischemic stroke have elevated blood levels of NR2 peptide/Ab that correlate with the amount of brain damage revealed through brain scans (MRI) and neurocognitive testing (Dambinova SA, et al. Clin Chem 2003; 49:1752-1762).

NR2 peptides and antibodies may have diagnostic as well as prognostic utility in the acute management of patients with cerebrovascular accidents, TIA and stroke. The evaluation of the presence or absence of such markers in the acute setting may improve diagnostic/prognostic accuracy as well as define those patients at increased risk for subsequent stroke.

OBJECTS OF THE INVENTION

The medical community faces several principal diagnostic challenges in overall stroke management, including differentiating brain ischemic attack from hemorrhage and stroke like disorders, and evaluating the risk of stroke or other complicating factors. In the present invention, blood assays for detecting bound or total and unbound NR2 peptide were developed, and used to differentiate cerebrovascular accidents such as TIA and stroke from cerebral hemorrhage and stroke mimics.

Therefore, it is an object of the invention to unbound NR2 peptide test to evaluate acute cerebrovascular accidents and TIA/stroke as defined by DWI/MRI for better diagnosis, management and treatment.

It is another object of the present invention to detect bound or total NR2 peptide to accurately diagnose chronic TIA and stroke to the exclusion of stroke-like disorders in conjunction with NIHSS evaluations and neuroimaging.

It is still another object of the present invention to distinguish between new and old brain lesion areas and lacunar strokes defined by DWI, by measuring for increased concentrations of bound or total and unbound NR2 peptides above population norms.

Still another object of the invention is to help predict the likely occurrence of a subsequent cerebrovascular accident leading to progression to completed stroke based on concentrations of unbound and bound or total NR2 peptide.

Still another object of the invention is to help evaluate the severity of symptoms suggestive of potential TIA depending on concentrations of unbound and bound or total NR2 peptide.

It is another object of the present invention to evaluate infarction size based on DWI/MRI and concentrations/ratios of unbound and bound or total NR2 peptide.

It is another object of the present invention is to provide methods for real-time assessments of NR2 peptides and antibodies and ratios, and for determining therapeutic windows in patients with cerebrovascular accidents or TIA/stroke for timely neuroprotective therapy.

Still another object of the present invention is to provide diagnostic tests for detecting unbound and bound or total NR2 peptide as additional tools to neurological observations and neuroimaging in identifying patients who are at subsequently high risk in the near term of completed stroke.

SUMMARY OF THE INVENTION

It has been unexpectedly discovered that levels of circulating NR2 peptides that are bound to immunoglobulins, albumin and other peptide carriers in the blood (hereinafter "bound NR2 peptides"), which are not detected in conventional NR2 test kits or testing regimens, provide useful diagnostic information to clinicians evaluating TIA and stroke and stroke-like disorders and brain damage underlying these cerebrovascular events. The detection and quantification of these bound NR2 peptides can be used to diagnose the existence of brain lesions resulting from insufficient blood circulation or microembolic events, and can greatly increase the accuracy of diagnoses and subsequent treatment efficacy, especially when used in combination with other diagnostic tests such as tests for unbound NR2 peptides, NIHSS scoring and neuroimaging.

The rapid evaluation of these brain markers in emergency room settings will greatly enhance the physicians' ability to identify patients who are suffering an acute cerebrovascular event such as TIA or stroke, and help physicians determine whether a cerebrovascular event is an ischemic event, a hemorrhagic stroke or a stroke-like disorder. In emergency rooms and every doctor's office, the use of the brain markers will help identify patients at risk for having an ischemic stroke, and assist in the development of neuroprotective regimens.

It has been determined experimentally that total NR2 peptide concentrations greater than about 2.0 ng/ml (i.e. bound and unbound peptides) are above the norm for healthy individuals, and portend an unhealthy cerebrovascular state, especially when combined with a level of unbound NR2 peptides above the norm for healthy individuals (i.e. greater than about 0.5-0.6 ng/ml). When evaluating a patient suffering from a neurological deficit, a comparison of concentrations of total and unbound peptide concentrations has remarkable diagnostic capacity to determine whether the underlying ischemic is a recurrent episode or flare-up of a chronic condition, or whether the patient is experiencing a primary cerebrovascular accident. In particular, the combination of (1) a total peptide concentration greater than about 2.0 ng./ml. and (2) a total:unbound peptide ratio greater than about 2:1 correlates well with a recurrent event, especially when combined with an unbound peptide concentration less than about 2.0, 1.0, 0.8, 0.6 or 0.5 ng/ml. In contrast, a combination of (1) an unbound peptide concentration greater than about 1.0 ng./ml. and a total:unbound peptide ratio less than about 2:1, correlates well with a primary event, especially when combined with a total peptide concentration less than about 3.0 or 2.0 ng./ml.

Once again, these correlations can be extensively used for the choice of emergency treatment such as anti-platelet or neuroprotective therapy in a short time frame. The biomarker profile provides real time evidence of a cerebrovascular accident, and the reduction in concentration of circulating total NR2 peptide correlates well with positive effect of chosen therapy. The methods of the present invention also can be employed in a primary care setting, when evaluating a cerebrovascular accident or TIA, and in identifying patients who are at subsequently high risk in the near term of TIA or completed stroke. In addition, based upon results showing an increased risk of suffering TIA or stroke, prevention therapy can be administered, and the effectiveness of the therapy monitored using the methods of the present invention.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

The accompanying drawing, which are incorporated in and constitute a part of this specification, illustrate several embodiments of the invention and together with the description, serve to explain the principles of the invention.

DETAILED DESCRIPTION OF THE INVENTION

The present invention may be understood more readily by reference to the following detailed description of preferred embodiments of the invention and the Examples included therein.

Definitions and Use of Terms

As used in this specification and in the claims which follow, the singular forms "a," "an" and "the" include plural referents unless the context clearly dictates otherwise. Thus, for example, reference to "a fragment" includes mixtures of fragments, reference to "an cDNA oligonucleotide" includes more than one oligonucleotide, and the like.

"Polypeptide," "protein" and "peptide" are used interchangeably herein and include a molecular chain of amino acids linked through peptide bonds. The terms do not refer to a specific length of the product. Thus, "peptides," "oligopeptides," and "proteins" are included within the definition of polypeptide. The terms include post-translational modifications (isoforms) of the polypeptide, for example, glycosylations, acetylations, phosphorylations, chelates, and the like. In addition, protein fragments, analogs, mutated or variant proteins, chimeric peptides and the like are included within the meaning of polypeptide. The polypeptide, protein and peptides may be in cyclic form or they may be in linear form.

An NMDA receptor or NMDAR is one of a family of ligand-gated ion channels that bind preferentially to N-methyl-D-aspartate and that mediate the vast majority of excitatory neurotransmission in the brain (Dingledine R. et al., Pharmacol Rev. 1999 March; 51(1):7-61.). The receptors include subunits reported in the literature as NR1, NR2A, NR2B, NR2C, NR2D, NR3A and NR3B, that perform distinct pharmacological functions. GenEMBL Accession Nos. have been reported for NR1 (X58633), NR2A (U09002) and NR2B (U28861), and are described in WO 02/12892 to Dambinova.

An NMDA receptor peptide refers to a full length NMDA receptor protein, a peptide fragment of the naturally or synthetically occurring full length NMDA receptor, or an anologue or isoform thereof. An NR2 peptide thus includes the full length NR2A, NR2B, NR2C and NR2D subunits, in addition to fragments, analogs and derivatives thereof. Similarly, an NR2A, NR2B, NR2C, or NR2D peptide means the full length naturally occurring NR2A, NR2B, NR2C or NR2D peptide subunits, or a fragment, analog or derivative thereof. The N-terminal domain of NMDA peptides refers to the amino acid N-terminal domain fragment of the full length peptide, or a fragment, analog or derivative thereof, typically about 40 or 50 amino acids long, but as much as 150, 200 or 300 amino acids long, as described in WO 02/12892 to Dambinova.

An "analogue" of a peptide means a peptide that contains one or more amino acid substitutions, deletions, additions, or rearrangements. For example, it is well known in the art of protein biochemistry that an amino acid belonging to a grouping of amino acids having a particular size or characteristic (such as charge, hydrophobicity, and hydrophilicity) can often be substituted for another amino acid without altering the activity of the protein, particularly in regions of the protein that are not directly associated with biological activity. Thus, an analogue of an NMDA peptide is useful in the present invention if it includes amino acid substitutions, deletions, additions or rearrangements at sites such that antibodies raised against the analogue are still specific against the NMDAR peptide.

Unless stated to the contrary, an NMDAR analogue or mutant as used in this document refers to a sequence that has at least 80% amino acid identity with naturally occurring NMDA, although it could also contain at least 85%, 90%, or 95% identity. Amino acid identity is defined by an analogue comparison between the analogue or mutant and naturally occurring NMDA. The two amino acid sequences are aligned in such a way that maximizes the number of amino acids in common along the length of their sequences; gaps in either or both sequences are permitted in making the alignment in order to maximize the number of common amino acids. The percentage amino acid identity is the higher of the following two numbers: (1) the number of amino acids that the two peptides have in common with the alignment, divided by the number of amino acids in the NMDA analogue, multiplied by 100, or (2) the number of amino acids that the two peptides have in common with the alignment, divided by the number of amino acids in naturally occurring NMDA peptide, multiplied by 100. Amino acids appended to the ends of the fragment under analysis are not taken into consideration.

NMDA derivatives include naturally occurring NMDA and NMDA analogues and fragments thereof that are chemically or enzymatically derivatized at one or more constituent amino acids, including side chain modifications, backbone modifications, and N- and C-terminal modifications, by for example acetylation, hydroxylation, methylation, amidation, phosphorylation or glycosylation. The term also includes NMDA salts such as zinc NMDA and ammonium NMDA.

The term "antibody" is synonymous with "immunoglobulin." As used herein, the term "antibody" includes both the native antibody, monoclonally generated antibodies, polyclonally generated antibodies, recombinant DNA antibodies, and biologically active derivatives of antibodies, such as, for example, Fab', $F(ab')_2$ or Fv as well as single-domains and single-chain antibodies. A biologically active derivative of an antibody is included within this definition as long as it retains the ability to bind the specified antigen. Thus, an NR2 antibody that binds specifically to an NR2 peptide has the ability to bind at least one NR2 peptide.

The term "NR2" peptide refers to any peptide expressed in the NR2 subfamily of NMDA receptors, including full length NR2A, NR2B, NR2C and NR2D subunits, fragments thereof, and recombined fragments thereof. A preferred NR2 peptide for practicing the present invention is recombined from sequences within the NR2A and NR2B subunits, or analogs thereof. The sequences are preferably autoantigenic, and preferably derive from the N-terminal domain of the recited NMDA receptor subtype. The peptides are preferably less than about 40 amino acids in length, and greater than about 15 amino acids. It will of course be understood that analogs of such sequences may also be present in the recombinant peptide.

A preferred NR2 peptide is a recombinant NR2A/NR2B peptide, and has the following nucleotide sequence:
NGMIGEVVYQRAVMAVGSLTIKRIVTEKTD 31

A "protein detergent" refers to any compound capable of freeing NR2 peptides from circulating complexes in the human blood stream, including various ionic surfactants and amphiphilic molecules that are generally known in the art. Examples include sodium dodecyl sulfate (a/k/a sodium lauryl sulfate), sodium taurocholate, sodium cholate, CTAB, LDAO, CHAPS, Tween 20, Thesit, Triton X-100, NP40, n-octyl sucrose, n-dodecyl sucrose, n-dodecyl maltoside, octyl glucoside, octyl thioglucoside, n-hexyl glucoside and n-dodecyl glucoside.

General Discussion

The present disclosure describes diagnostic and therapeutic applications that result from the realization that genetic or accidental increase of NMDA receptors synthesis in the brain reflects a neurological ischemic deficit, and may be used for fast diagnosis of stroke or TIA and to distinguish from other stroke-like disorders. NMDA receptors that are abnormally expressed in the brain are quickly metabolized and, following penetration of the blood brain barrier, these metabolic destruction products enter the circulatory system. The immune system recognizes these peptides and protein fragments as foreign antigens and responds by generating antibodies and immune complexes. Once bound in these immune complexes, and other agglomerates such as albumin complexes in the bloodstream, these peptides are largely unavailable for detection in conventional testing regimens. In the present invention the content of bound NR2 peptide (bound antigen) or total NR2 peptide, and optionally unbound NR2 peptide (free antigen), are evaluated as brain biomarkers for their prognostic/diagnostic value when evaluating cerebrovascular accidents, TIA and stroke, and the risk of future cerebrovascular accidents, TIA and stroke.

Thus, in one aspect the present invention provides a method for diagnosing a central nervous system disorder comprising measuring amounts of bound or total NR2 peptide or NMDA receptors fragments in a biological sample, and optionally measuring unbound NR2 peptide. In another embodiment, the invention provides A method for determining the pathological origin of a neurological deficit comprising: (a) providing a patient suffering from a neurological deficit; (b) detecting and quantifying bound or total NR2 peptide in a biological fluid from said patient to arrive at a quantity of bound or total NR2 peptide; and (c) comparing said quantity of bound or total NR2 peptide with a population norm for bound or total NR2 peptide in said biological fluid in apparently healthy human subjects. In a particularly preferred embodiment, the method further comprises: (a) detecting and quantifying unbound NR2 peptide in a biological fluid from said patient to arrive at a quantity of unbound NR2 peptide; and (b) comparing said quantity of unbound NR2 peptide with a population norm for unbound NR2 peptide in said biological fluid in apparently healthy human subjects.

Elevated levels of NR2 peptide are specific to brain damage, and are expressed in ischemic brain tissue at higher rates than other NMDA receptors, and thus are uniquely suited for assessing cerebral ischemic episodes, TIA and stroke. Baseline levels for determining whether the measured concentrations of unbound and bound or total NR2 peptide are elevated, and hence indicative of a central nervous system disorder, can be obtained from population norms or, preferably, from a patient's own test history.

Immunoassay techniques are generally preferred for measuring the proteins or peptides of the present invention, although other analytical techniques are also available as known to those skilled in the art, such as HPLC. However, when using immunoassays it has been found that the antigenic determinants are concentrated in the N-terminal domain of the NR2 type of NMDA receptor, and that antibodies rose against the N-terminal domains and fragments thereof should be employed for optimal test results.

The methods of the present invention are preferably performed by directly measuring the concentrations of unbound and bound or total NR2 peptides in a selected biological sample, using immunoassay techniques employing antibodies raised against the biomarkers by direct ELISA, or through quantitative techniques such as HPLC. If unbound and bound or total NR2 peptides are measured, they are preferably measured using one or more antigenic fragments of the NR2 peptide as the target of the antibody, as opposed to a whole NR2 type of NMDA receptor. Healthy persons generally have unbound NR2 peptide blood concentrations less than about 2.0, 1.0, 0.8, 0.6 or 0.5 ng/ml and total NR2 peptide blood concentrations less than about 3.0, 2.0 or 1.5 ng/ml.

The methods of the present invention can be performed using practically any biological fluid where circulating cerebral NMDA receptors, or markers of such receptors, are expressed or found, including blood, urine, blood plasma, blood serum, cerebrospinal fluid, saliva, perspiration or brain tissue. In a preferred embodiment the biological fluid is plasma or serum, and in an even more preferred embodiment the plasma or serum is diluted to a ratio of about 1:50.

Emergency Room Diagnosis and Rehabilitation Prognosis

As mentioned above, the methods of the present invention are especially well suited for use in emergency room setting because NR2 peptide or NMDA receptor fragments levels are elevated at a very fast and early stage of ischemic events and thus provide a real time indication of brain damage especially when measured in conjunction with NIHSS and CT or DWI// MRI. In a preferred embodiment, the patient is evaluated while the ischemic event is ongoing, preferably in time to intervene with neuroprotective therapy. Thus, for example, the patient may be evaluated while experiencing a neurological deficit. Alternatively, the patient may be evaluated within about 6, 5, 4, 3, 2 or even fewer hours after initial onset of stroke-like symptoms. Therefore, in one embodiment the invention provides a method for evaluating brain status by blood tests, or the existence of a central nervous system disorder such as cerebrovascular accident, TIA or stroke, by withdrawing the biological sample from a human within three hours of the onset of stroke-like symptoms.

The methods of the present invention are also especially useful in an emergency room setting when adapted to a latex agglutination assay, because of the speed and ease with which the latex agglutination procedure can be employed. Using the latex agglutination processes bedside, a care provider can often obtain blood test results in less than 10 minutes. Thus, using the methods of the present invention real-time data can be obtained even in the "field" during patient transportation, that will offer a greater window of time for neuroprotective treatment. Therefore in still another embodiment of the invention, the amount of time elapsed between withdrawing the biological sample from the subject, and detecting or measuring the presence or quantity of unbound and bound or total NR2 peptide or NMDA receptor fragments, is less than 30 minutes.

One of the most pronounced advantages of the present invention is the ability to distinguish ischemic episodes such as stroke from other stroke-like disorders such as brain tumor, traumatic brain injury, abscess, air embolism, giant cell arteritis, collagen vascular diseases, metabolic abnormalities, Bell's palsy, labyrinthitis, or demyelinating diseases. This advantage is available regardless of whether the peptide detected is bound or unbound, and this aspect of the invention applies to regardless of whether the peptide detected is bound or unbound, or whether both peptides are detected. In particular, if a stroke is suspected, the method will help diagnose whether the stroke is an ischemic or hemorrhagic insult, and guide the practitioner toward a neuroprotective therapy that is suited to the type of stroke diagnosed. Thus, in another embodiment the invention provides a method for diagnosing the existence of a cerebrovascular disorder, TIA or stroke further comprising, when the diagnosis confirms a stroke, evaluating from concentrations of unbound and/or bound or total NR2 peptide or NMDA receptor fragments whether the stroke is ischemic or hemorrhagic and administering ischemic or hemorrhagic stroke therapy as appropriate.

In one embodiment the therapy under consideration is tissue plasminogen activator (tPA), and the invention provides a method of diagnosing and treating cerebral ischemia comprising: (a) providing a patient suffering from a neurological deficit; (b) detecting and quantifying NR2 peptide (bound and/or unbound) in a biological fluid from said patient to obtain a first quantity of NR2 peptide; (c) comparing said first quantity of NR2 peptide with a population norm for NR2 peptide in said biological fluid in apparently healthy human subjects; (d) administering tPA to said patient if said first quantity of said NR2 peptide is above the population norm for NR2 peptide in said biological fluid in apparently healthy human subjects; and (e) not administering tPA to said patient if said quantity of said NR2 peptide is below the population norm for NR2 peptide in said biological fluid in apparently healthy human subjects. In a preferred embodiment, bound or total and unbound NR2 peptide are separately detected and quantified to arrive at quantities of bound or total and unbound NR2 peptides, and said quantities of said bound or total and unbound NR2 peptide are compared with population norms of bound or total and unbound NR2 peptides in said biological fluid in apparently healthy human subjects.

In another embodiment, the method is performed by (a) evaluating said patient for acute facial paresis, arm drift, abnormal speech or other neurological deficit; (b) administering tPA to said patient if said acute facial paresis, arm drift, or abnormal speech is observed and said quantity of said NR2 peptide is above the population norm for NR2 peptide in said biological fluid in apparently healthy human subjects; and (c) not administering tPA to said patient if said acute facial paresis, arm drift, or abnormal speech is not observed and said quantity of said NR2 peptide is below the population norm for NR2 peptide in said biological fluid in apparently healthy human subjects.

Moreover, one can periodically repeat the procedure to provide continuous monitoring of a patient's state as a follow up to treatment or to monitor the efficacy of a particular therapeutic regime. In this embodiment, it is preferable for the mammal to be concurrently undergoing treatment for the disorder. More preferably, the samples are collected at intervals from about 20 min to about 1 month. Even more preferably, the interval is from about 20 min to about 2 hours. Most preferably the samples are collected at an interval of about 30 minutes. Thus, in still another embodiment the invention provides a method for diagnosing the progression of cerebrovascular disorder, TIA or stroke further comprising measuring the presence or quantity of unbound and bound or total NR2 peptide and/or NMDA receptor fragments in a biological sample one or more additional times, at a frequency of less than about 6 hours. Once again, this testing is preferably performed in conjunction with NIHSS evaluations and neuroimaging. Put another way, in a still further embodiment, NR2 peptide is detected and quantified in a biological fluid from said patient a second time to obtain a second quantity of NR2 peptide; said second quantity of NR2 peptide is compared to said first quantity; tPA is administered a second time to said patient if the second quantity is greater than the first quantity; and tPA is not administered a second time to said patient if said second quantity is not greater than the first quantity.

Primary Care Physician Setting

In another application the method is used in a clinical setting to identify individuals who are at high risk in the near term of suffering a stroke, or to monitor the effectiveness of risk reducing therapies. A number of therapies can be employed to reduce the risk of stroke in an individual. The use of antiplatelet agents, particularly aspirin, is a standard treatment for patients at risk for stroke. People with atrial fibrillation (irregular beating of the heart) may be prescribed anticoagulants. When a treatment is prescribed, the methods provide a novel method for determine the efficacy of the therapy.

Therefore, in one embodiment the invention provides a method for evaluating an individual's risk for TIA or stroke comprising measuring levels of bound or total (and optionally unbound) NR2 peptide and/or NMDA receptor fragments thereof in a biological sample from the individual, and comparing the concentrations detected to a baseline level. In one embodiment the baseline levels are derived from population averages. In another embodiment the baseline levels are derived from the individual's own medical history in conjunction with NIHSS and DWI/MRI data.

In another embodiment the method is performed more than once to monitor the reduction or increase in risk for stroke or TIA, optionally in conjunction with the administration of risk reduction therapy (neuroprotective strategy). In one embodiment the method is performed at a frequency of from about once a week to about once in six months. In another embodiment the method is performed at a frequency of from about once in a month to about three months.

Pre-Surgery Risk Assessment

In still another embodiment the invention provides a method for aiding in the assessment of the risk of stroke in an apparently healthy human subject prior to surgery. When a patient is tested and has dangerous levels of bound or total NR2 peptides in his or her bloodstream, it is preferred to test the patient several more times before surgery and during surgery. In addition, because patients often do not suffer an adverse neurological event until shortly after the surgery, it is preferred to test these patients one or more additional times after surgery, within one or more of the following time periods: one hour, three hours, six hours, twelve hours, twenty four hours, three days, seven days, or thirty days.

The methods can be performed on adults or children scheduled for surgery, and are particularly useful when evaluating patients who are already predisposed to suffering a neurological event, such as patients with a history of diabetes, atherosclerosis, high blood pressure, or a previous suspected or confirmed TIA or stroke. The methods can also be used in conjunction with MMSA testing, before surgery, to predict the risk of an adverse neurological event. Preoperative decreased MMSA component scores for orientation, attention and recall have been associated with confusion and cerebrovascular events shortly after surgery.

The types of neurological events that can be predicted by the current invention are generally those induced by cerebral ischemia, and especially ischemic events that are caused by insufficient supplies of oxygen to the brain (as opposed to hemorrhagic events that occur when blood vessels are ruptured in the brain). These events can be focalized in a particular region of the brain, as occurs in stroke or TIA, or global, as occurs in delirium. The adverse neurological event may thus be characterized by confusion or may be diagnosed as a TIA or ischemic stroke. Oxygen supplies can be compromised due to the health condition of the patient (as in certain blood disorders such as anemia), but more commonly will be caused by the surgical event. The adverse neurological event is said to be "from" the surgery if the event occurs during surgery, or within thirty days after the surgery is completed, although the resulting adverse event could also be identified in a time frame of seven days, three days, two days or one day, if desired.

The prognostic methods of the present invention can predict the risk of adverse neurological events from any type of surgery, although traumatic surgeries that temporarily slow or halt the flow of oxygen to the brain will benefit most, For example, the method should be performed before any cardiovascular procedure that occludes or blocks normal blood circulation, that results in intraoperative micro- or macro-emboli, abnormal cerebral perfusion, reperfusion injury, or an inflammatory or neruhumoral response. The invention is especially useful in predicting the occurrence of adverse neurological events when a cardiopulmonary bypass is performed.

Diagnostic Platforms

The diagnostic methods for measuring bound or total NR2 peptide usually require the bound peptide to be stripped from any complexes in the bloodstream where the peptide is present, such as immunoglobulin and albumin complexes. This stripping is typically accomplished through the use of a protein detergent. Thus, in one embodiment, the invention provides a test kit for detecting and quantifying bound or total NR2 peptide in a biological sample comprising: (a) an antibody reagent comprising antibodies that are capable of specifically binding NR2 peptide in a test sample; (b) a protein detergent; and (c) an indicator reagent. In another embodiment the invention provides a method for detecting and quantifying bound or total NR2 peptide in a biological sample comprising: (a) contacting a biological sample with a protein detergent to yield a denatured biological sample; (b) contacting said denatured biological sample with an antibody reagent comprising antibodies that are capable of specifically binding NR2 peptide in a test sample, for a time sufficient to allow formation of bound complexes between said NR2 peptide and said antibody; and (c) detecting and quantitating said bound complexes.

The diagnostic methods of the present invention can be performed using any number of known diagnostic techniques, including direct or indirect ELISA, RIA, immunodot, immunoblot, latex aggutination, lateral flow, fluorescence polarization, and microarray. In one particular embodiment, the invention is practiced using an immobilized solid phase for capturing and measuring the NMDAR peptide marker. Therefore, in one embodiment the methods of the invention comprise: (a) contacting a biological sample from the patient with an immobilized solid phase comprising a NMDAR peptide or antibody, for a time sufficient to form a complex between said NMDAR peptide or antibody and NMDAR antibody or peptide in said biological sample; (c) contacting said complex with an indicator reagent attached to a signal-generating compound to generate a signal; and (d) measuring the signal generated. In a preferred embodiment, the indicator reagent comprises chicken anti-human or anti-human IgG attached to horseradish peroxidase.

In a preferred embodiment, the solid phase is a polymer matrix. More preferably, the polymer matrix is polyacrylate, polystyrene, or polypropylene. In one preferred embodiment the solid phase is a microplate. In another preferred embodiment, the solid phase is a nitrocellulose membrane or a charged nylon membrane.

In another embodiment, the method is performed using agglutination. Therefore, in still another embodiment the invention comprises: (a) contacting a biological sample from the patient with an agglutinating carrier comprising a NMDAR peptide or antibody, for a time sufficient to form an agglutination complex between said NMDAR peptide or antibody and NMDAR antibody or peptide in said biological sample; (c) generating a signal from the agglutination; (d) correlating said signal to said levels of one or more markers of NMDAR peptide or antibody. In a preferred embodiment, the "sufficient time" is less than 30, 20, 15 or even 10 minutes.

Latex agglutination assays have been described in Beltz, G. A. et al., in Molecular Probes: Techniques and Medical Applications, A. Albertini et al., eds., Raven Press, New York, 1989, incorporated herein by reference. In the latex agglutination assay, antibody raised against a particular biomarker is immobilized on latex particles. A drop of the latex particles is added to an appropriate dilution of the serum to be tested and mixed by gentle rocking of the card. With samples lacking sufficient levels of the biomarkers, the latex particles remain in suspension and retain a smooth, milky appearance. However, if biomarkers reactive with the antibody are present, the latex particles clump into visibly detectable aggregates.

An agglutination assay can also be used to detect biomarkers wherein the corresponding antibody is immobilized on a suitable particle other than latex beads, for example, on gelatin, red blood cells, nylon, liposomes, gold particles, etc. The presence of antibodies in the assay causes agglutination, similar to that of a precipitation reaction, which can then be detected by such techniques as nephelometry, turbidity, infrared spectrometry, visual inspection, colorimetry, and the like.

The term latex agglutination is employed generically herein to refer to any method based upon the formation of detectable agglutination, and is not limited to the use of latex as the immunosorbent substrate. While preferred substrates for the agglutination are latex based, such as polystyrene and polypropylene, particularly polystyrene, other well-known substrates include beads formed from glass, paper, dextran, and nylon. The immobilized antibodies may be covalently, ionically, or physically bound to the solid-phase immunoadsorbent, by techniques such as covalent bonding via an amide or ester linkage, ionic attraction, or by adsorption. Those skilled in the art will know many other suitable carriers for binding antibodies, or will be able to ascertain such, using routine experimentation.

Conventional methods can be used to prepare antibodies for use in the present invention. For example, by using a peptide of a NMDA protein, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be administered and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for NMDAR proteins or fragments as described herein.

In one embodiment the method is practiced using a kit that has been calibrated at the factory based upon antibodies purified from human blood. Therefore, in another embodiment the invention is practiced under the following conditions: (a) NMDAR antibody levels in said biological fluid are measured using a diagnostic kit; (b) said diagnostic kit comprises bound NMDAR peptides; and (c) said kit is manufactured against an antibody standard comprising a fraction of immunoglobulins G purified from human blood.

In addition, the method can be practiced using commercially available chemiluminescence techniques. For example, the method could employ a two-site sandwich immunoassay using direct chemiluminescent technology, using constant amounts of two monoclonal antibodies. The first antibody, in a fluid reagent, could be an acridinium ester labeled monoclonal mouse anti-human NMDA receptor peptide BNP $(F(ab')_2$ fragment specific to a first portion of the peptide. The second antibody, in the solid phase, could be a biotinylated monoclonal mouse anti-human antibody specific to another portion of the peptide, which could be coupled to streptavidin magnetic particles. An immuno-complex would be formed by mixing a patient sample and the two antibodies. After any unbound antibody conjugates are washed away, the chemiluminescence of the immuno-complex signal could then be measured using a luminometer.

When the NMDA receptors are detected indirectly, by measuring the cDNA expression of the NMDA receptors, the measuring step in the present invention may be carried out by traditional PCR assays such as cDNA hybridization, Northern blots, or Southern blots. These methods can be carried out using oligonucleotides encoding the polypeptide antigens of the invention. Thus, in one embodiment the methods of this invention include measuring an increase of NMDAR cDNA expression by contacting the total DNA isolated from a biological sample with oligonucleotide primers attached to a solid phase, for a sufficient time period. In another preferred embodiment, NMDAR cDNA expression is measured by contacting an array of total DNA bound to a solid matrix with a ready-to-use reagent mixture containing oligonucleotide primers for a sufficient time period. Expressed NMDAR cDNA is revealed by the complexation of the cDNA with an indicator reagent that comprises a counterpart oligonucleotide to the cDNA attached to a signal-generating compound. The signal-generating compound is preferably selected from the group consisting of horseradish peroxidase, alkaline phosphatase, urinase and non-enzyme reagents. The signal-generating compound is most preferably a non-enzyme reagent.

The immunosorbent of the present invention for measuring levels of autoantibody can be produced as follows. A fragment of the receptor protein is fixed, preferably by covalent bond or an ionic bond, on a suitable carrier such as polystyrene or nitrocellulose. If the standard polystyrene plate for immunological examinations is employed, it is first subjected to the nitration procedure, whereby free nitrogroups are formed on the plate surface, which are reduced to amino groups and activated with glutaric dialdehyde serving as a linker. Next the thus-activated plate is incubated with about 2 to 50 nM of the target peptide for the purpose of chemically fixing the respective immunogenic fragment of the receptor protein for a time and at a temperature sufficient to assure fixation (i.e. for about 16 hours at 4° C.).

It is also practicable to produce the immunosorbent by fixing the respective fragment of the receptor protein on nitrocellulose strips by virtue of ionic interaction. The respective fragment of the receptor protein isolated from the mammals' brain is applied to nitrocellulose and incubated for 15 min at 37° C. Then nitrocellulose is washed with a 0.5% solution of Tween-20, and the resultant immunosobent is dried at room temperature and stored in dry place for one year period.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Patient Groups Studied

Forty one adult patients with symptoms suggestive of a possible transient ischemic attack and at high risk in the near term for a completed stroke (Table 1) were evaluated. Exclusion criteria included those patients whose symptoms resolved after treatment with glucose and were likely suffering from hypoglycemia.

During routine evaluation of the patient, the evaluating physician verified the presence or absence of five factors including: age >60, diabetes mellitus, TIA symptoms >10 minutes, weakness, speech impairment. After informed consent, blood samples were collected on the day of admission from all subjects. Patients were then followed-up approximately ninety days after presentation via telephone, personal interview, or review of medical records to assess for recurrent TIA or stroke. Stroke was defined as having occurred if a patient developed a permanent neurological deficit or new radiographic (CT or MRI) evidence of central nervous system infarct correlating with the patient's symptom onset during the ninety days following initial evaluation. The multi-sequence MR imaging protocol, which included DW1, T2WI and MRA, was performed as a single session within 24 hours after symptom onset. The following CT imaging data were recorded: location of hemorrhage, hemorrhage volume, and presence of intraventricular blood or mass effect. The amounts of unbound NR2 peptide were determined in plasma of the above described patients and an age-matched group of healthy volunteers (n=10).

One patient was excluded after showing basal ganglia growth and being diagnosed with a brain tumor (Table 1). 42% of patients underwent MRI examination within 3 hours of symptom onset, and 79% of patients underwent CT scanning within 3 hours of symptom onset.

TABLE 1

Demographic Characteristics of patients

| Characteristics | Baseline |
| --- | --- |
| Mean age, y | 65.0 |
| Men, n | 20 |
| Left side of body event, n | 13 |
| Mean initial blood glucose, mg/dL | 151 |

Example 2

Unbound NR2 Peptide as a Marker of New Brain Lesions

Figure 1:
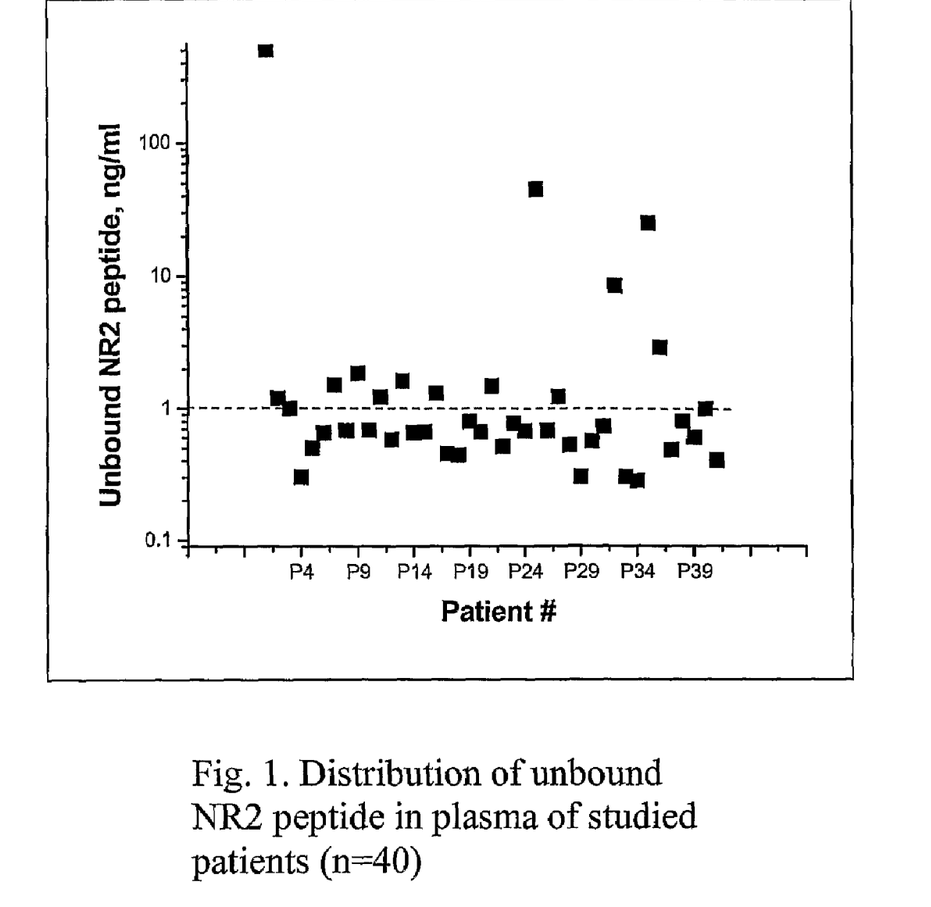
FIG. 1 is a graphical depiction of the distribution of unbound NR2 peptide in plasma of patients studied (n=40) in the examples of the present invention.

Concentrations of unbound NR2 peptide in blood were obtained by direct ELISA as presented in Table 2. The distribution of unbound NR2 peptide depicted in FIG. 1 showed that patients with values of unbound NR2 peptide below 1.0 ng/ml (n=16) had no area of damage defined by CT/MRI (Table 1). The plasma of healthy persons had concentrations of unbound NR2 peptide ranging from 0.3 to 0.5 ng/ml.

TABLE 2

Unbound NR2 peptide in plasma of patients studied

| Subjects N | Unbound NR2 peptide range (min, max), ng/ml | Diagnosis | Neuroimaging modality: CT/MRI/DWI |
| --- | --- | --- | --- |
| 16 | 0.3-1.0 | CVA, radial & Bell's palsies, ICH | Negative or hemorrhage on CT |
| 14 | 1.0-44.0 | based on NIHSS: TIA, stroke | New lesions in cortex, subcortical areas, cerebellum, thalamus, lacunar |

Concentrations of unbound NR2 peptide above 1.0 ng/ml were detected in plasma of patients (n=14) with new ischemic lesions located in the cortex, basal ganglia, cerebellum and thalamus defined by DWI/MRI. (Table 2). In three patients with ischemic stroke (IS) abnormally elevated concentrations of unbound NR2 peptide allowed the diagnosis of lacunar infarcts that were then defined by DWI.

Example 3

Total NR2 Peptide as a Marker of Old Brain Lesions

Serum samples from 40 patients with suggestive TIA were analyzed for total NR2 peptide amounts (Table 3).

TABLE 3

Amounts of total NR2 peptide in serum of patients studied

| Subjects N | Total NR2 peptide range (min, max), ng/ml | Diagnosis | Neuroimaging modality CT/MRI/DWI |
| --- | --- | --- | --- |
| 17 | 0.9-2.0 | CVA, radial & Bell's palsies, ICH | Negative or hemorrhage on CT |
| 14 | 2.4-24.0 | based on NIHSS: TIA, stroke | Old parietal infarct, mid white matter, lateral ventricle, MCA area |

Figure 2:
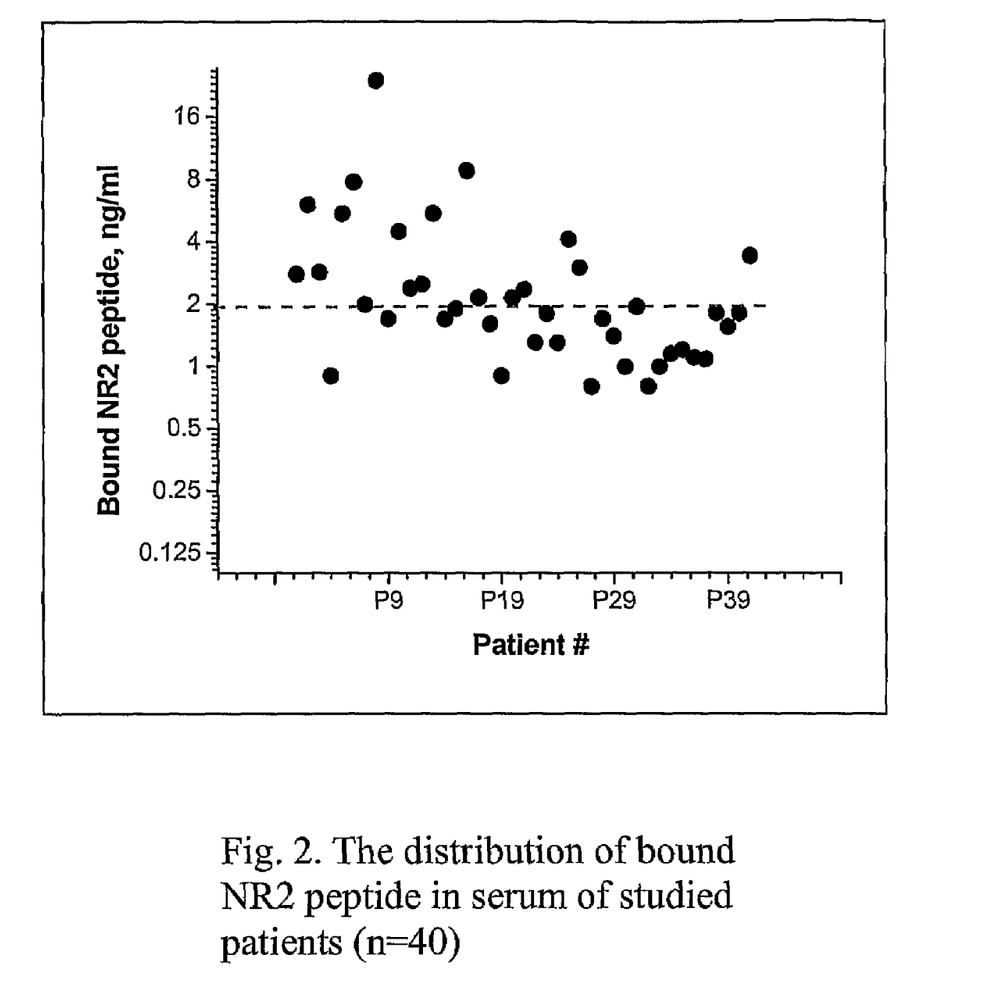
FIG. 2 is a graphical depiction of the distribution of total NR2 peptide in plasma of patients studied (n=40) in the examples of the present invention.
Figure 3:
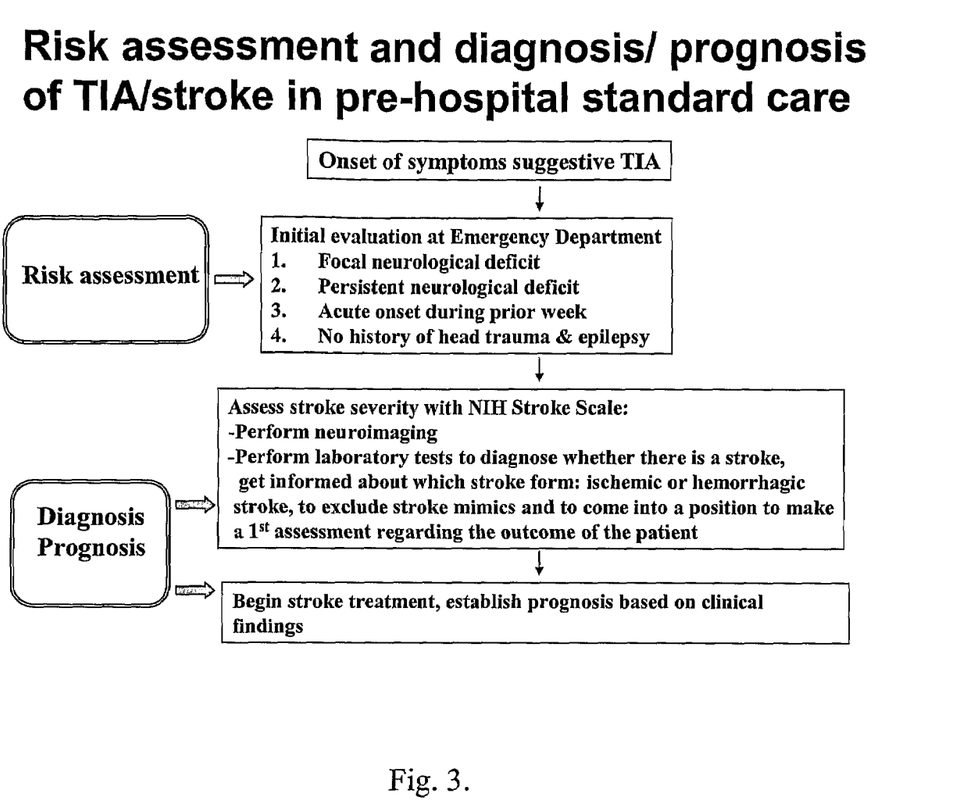
FIG. 3 is a flow chart diagramming the proposed standard of care for patients presenting with symptoms of TIA and/or stroke in an emergency room setting.
Figure 4:
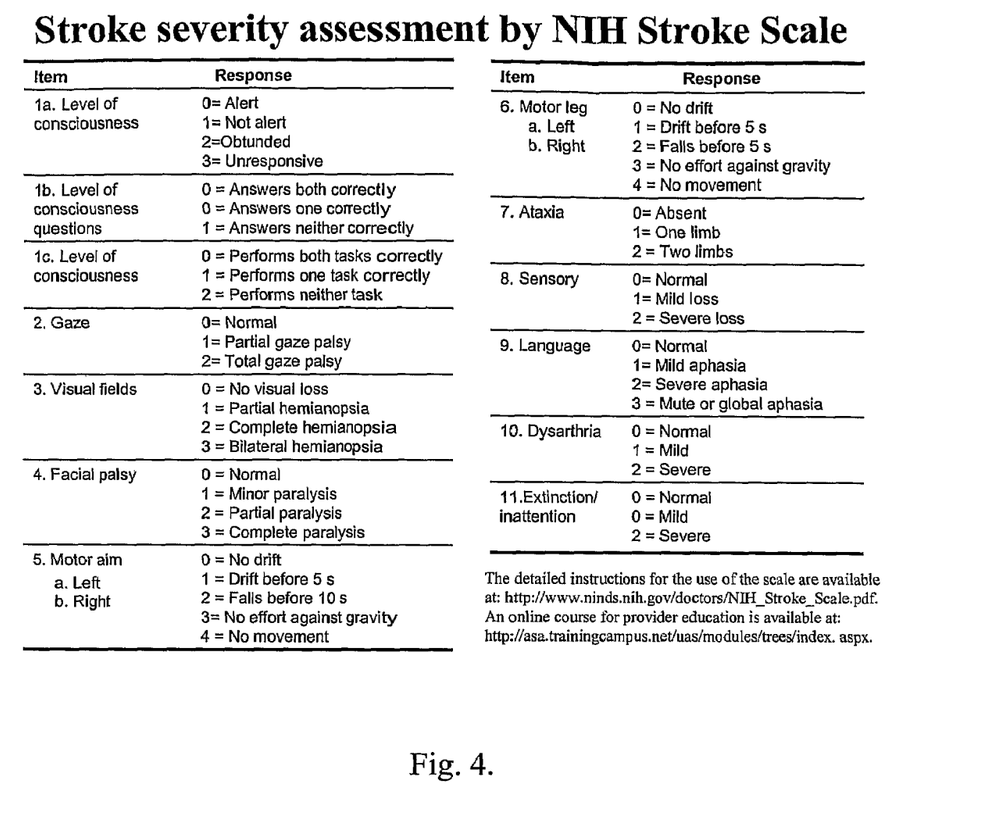
FIG. 4 is a diagram of the various factors and neurological deficits that are addressed when diagnosing stroke incidence and severity using the National Institutes of Health Stroke Scale ("NIHSS").

The statistical analysis of data showed that most patients had total NR2 peptide concentrations below 2.0 ng/ml (FIG. 2). Healthy persons had total NR2 peptide concentrations of 1.0-1.5 ng/ml. Neuroimaging of patients did not show abnormalities except for those with ICH. Concentrations of total NR2 peptide were >2.4 ng/ml in patients with previous history of cerebral ischemia and old infarction areas defined by MRI (Table 3). Nine patients out of 40 were clinically diagnosed as having recurrent TIA or stroke.

Example 4

Unbound and Total NR2 Peptide in Patients with TIA/Stroke (Primary and Recurrent Symptoms)

The simultaneous detection of unbound and total NR2 peptide allowed differentiation of patients with recurrent TIA/stroke from patients having new areas of infarction. Table 3 presents gives clinical diagnoses in patients based on CT/MRI/DWI, compared to their total and unbound NR2 peptide levels. Patients (n=14) with infarction areas on MRI/

DWI had "old" areas of lesions and a ratio of unbound:total peptides of less than 1:2 (Table 3, cases 3, 13, 16, 21).

TABLE 3

Unbound/total NR2 peptide in patients studied

| | NR2 peptide, ng/ml | | | |
|---|---|---|---|---|
| Case | Unbound | Total | Ratio | CT/MRI/DWI |
| 3 | 1.1 | 2.85 | 1:2.6 | Old right MCA stroke on CT and MRI |
| 13 | 1.22 | 2.4 | 1:2.0 | Small infarctions in pontomidcephalic region |
| 16 | 1.30 | 8.8 | 1:6.8 | MRI showed lacunar infarcts |
| 21 | 1.11 | 2.35 | 1:2.0 | Old parietal infarct and some lacunar infarcts on DWI |
| 32 | 8.3 | 0.8 | 10:1 | Acute left cerebellar infarction (new) |
| 35 | 24.5 | 1.2 | 20:1 | Acute left upper pons lesions (new) |

The patients who had drastically increased unbound NR2 peptide in plasma all had total peptide concentrations below 2.0 mg/ml, and all suffered from acute stroke with new areas of lesions defined by MRI/DWI (Table 3, cases 32, 35). The ratio of unbound:total NR2 peptides in the two patients were both greater than 2:1.

Example 5

The Correlation of Unbound/Total NR2 Peptide with NIHSS

On admission NIHSS scores were assessed in 40 patients who were then subdivided into two groups—those with NIHSS scores less than or equal to three, and those with NIHSS scores greater than three (Table 4). An MRA was completed in all patients; 24 of the 40 patients had evidence of flow abnormalities. There was no statistical difference in the proportion of patients who had CT or MRI within 3 hours of symptom onset or in the hemisphere of stroke between the NIHSS≦3 and the NIHSS>3 groups.

TABLE 4

Demographic Characteristics of NIHSS ≦ 3 with NIHSS > 3 Groups

| | NIHSS ≦ 3, (n = 26) | NIHSS > 3, (n = 14) |
|---|---|---|
| Mean age, y | 64.3 | 65.5 |
| Median NIHSS | 3 | 16 |
| Men, n | 11 | 9 |
| Left side of body event, n | 3 | 10 |
| Mismatch on MR, n | 2 | 6 (n = 11) |

Only 5 patients out of 24 patients had NIHSS scores less than or equal to three. None of these 5 patients had symptoms suggestive of a lacunar syndrome. Of the 5 patients, 4 had evidence of DWI changes. Unbound NR2 peptide above the 1.0 ng/ml cutoff was detected in the plasma of 3 patients (Table 5), while total NR2 peptide remained under the 2.0 ng/ml cut off for all persons who were diagnosed with TIA.

TABLE 5

Breakdown of 5 Patients With NIHSS < 3 + primary TIA

| | NR2 peptide, ng/ml | | NIHSS | |
|---|---|---|---|---|
| Case | Unbound | Total | Baseline | Hemisphere |
| 19 | 0.79 | 0.9 | 3 | Right |
| 38 | 1.50 | 2.0 | 2 | Left |
| 7 | 1.85 | 1.7 | 2 | Left |
| 9 | 2.85 | 1.1 | 3 | Right |
| 36 | 0.79 | 1.8 | 3 | Left |

The remaining 19 of 24 patients had NIHSS greater than three, and evidence of a DWI lesion at baseline. Within this group 5 patients were diagnosed with chronic TIA, and the remaining 14 patients were diagnosed as having acute IS. There was a significant correlation ($r_s$=0.92) between the NIHSS scores and values of unbound/total NR2 peptide. Patients later diagnosed as having acute IS (n=9) and NIHSS scores of 11-20 had unbound NR2 peptide levels approximately 3-44 times higher than levels observed in control subjects. The level of total NR2 peptide and median NIHSS scores had significant correlation ($r_s$=0.89) for patients with chronic TIA and recurrent IS (n=14).

Example 6

Unbound/Total NR2 Peptide in Patients with Stroke-Like Disorders

Within the group of persons evaluated who demonstrated TIA-like symptoms (n=16), two patients were diagnosed with Bell's and radial nerve palsies and three patients were diagnosed with intracerebral hemorrhage (ICH). In those patients unbound NR2 peptide was below the 1.0 ng/ml cutoff and total NR2 peptide was below the 2.0 ng/ml cutoff (Table 6). The preliminary diagnosis for case 34 was cerebrovascular disorder, but this diagnosis was changed to intracerebral hemorrhage after NR2 peptide testing and additional CT tests.

TABLE 6

Unbound/total NR2 peptide in patients with stroke-like disorders

| | NR2 peptide, ng/ml | | | |
|---|---|---|---|---|
| Case | Unbound | Total | Diagnosis | CT/MRI/DWI |
| 15 | 0.66 | 1.9 | Bell's palsy | Negative |
| 17 | 0.45 | 2.0 | ICH | ICH on CT |
| 24 | 0.67 | 1.3 | ICH | ICH on CT |
| 33 | 0.30 | 1.0 | Radial nerve palsy | Negative |
| 34 | 0.28 | 1.2 | ICH | ICH on CT |
| 27 | 1.21 | 0.8 | Bell's palsy changed to TIA | Left thalamus lacunar infarcts |
| 8 | 0.68 | 24.0 | Migraine changed to IS | Lacunar infarcts |

Case 27 showed unbound/total NR2 peptide under the corresponding cutoffs, but the preliminary diagnosis "Bell's palsy" was changed to "TIA" after DWI revealed lacunar infarct areas in thalamus. Case 8 was initially characterized as severe migraine but changed to ischemic stroke based on the results of total and unbound NR2 peptide testing. The DWI imaging detected lacunar lesions in the brain confirming the diagnosis of acute IS.

Example 7

Plasminogen Activator Treatment

A total of 13 patients with primary/chronic TIA and new/recurrent stroke were treated with plasminogen activator (tPA) within 24 h of admission (Table 7). Two patients had NIHSS scores less than three, were diagnosed as having primary TIA, and recovered within 24 h of admission without receiving thrombolytic therapy. Three patients received tpA in a dose of 66 mg after their NIHSS scores worsened by 1-2 points in the first 24 hours (cases 19, 36, 38).

Unbound NR2 peptide levels decreased substantially after tPA treatment (Table 8). The following assessment demonstrated their independency on the modified Rankin Scale at 3 months (Table 7).

TABLE 7

Patients treated with tPA

| N | Case | NIHSS Baseline | 24-h | Diagnosis | 3-month Rankin Scale Score |
|---|------|----------------|------|-----------|----------------------------|
| 1 | 19 | 3 | 3 | Primary | Independent |
| 2 | 38 | 2 | 4 | TIA | Independent |
| 3 | 36 | 5 | 7 | | Independent |
| 4 | 11 | 7 | 5 | Recurrent | Symptoms recurrence |
| 5 | 12 | 5 | 3 | TIA | Independent |
| 6 | 13 | 9 | 4 | | Independent |
| 7 | 32 | 15 | 12 | New cerebral | Independent |
| 8 | 35 | 18 | 14 | ischemia | Independent |
| 9 | 3 | 11 | 7 | Recurrent IS | Independent |
| 10 | 8 | 20 | 16 | | Independent |
| 11 | 10 | 17 | 14 | | Delirium at 2 mo. |
| 12 | 16 | 19 | 16 | | Independent |
| 13 | 25 | 16 | 12 | | Independent |

Patients with chronic TIA who had areas of lesion defined by DWI, and who did not show improvement in symptoms within 3 hours of admission, received intravenous tPA (66 mg) and this administration caused an improvement in NIHSS scores (Table 7). The clinical improvement was accompanied by a reduction of total and unbound NR2 peptide concentrations (Table 8). The most significant improvements in NIHSS scores were associated with greater reductions in total NR2 peptide concentrations compared to unbound NR2 peptide concentrations. Symptoms reoccurred for case 11 within three months.

TABLE 8

Alteration of unbound/total NR2 peptide after tPA administration

| N | Case | Unbound NR2 peptide ng/ml | | Total NR2 peptide, ng/ml | |
|---|------|---------|------|---------|------|
| | | Baseline | 24-h | Baseline | 24-h |
| 1 | 19 | 0.79 | 0.53 | 0.9 | 1.1 |
| 2 | 38 | 0.79 | 0.50 | 1.8 | 1.9 |
| 3 | 36 | 2.85 | 1.75 | 1.1 | 1.4 |
| 4 | 11 | 1.22 | 1.1 | 2.4 | 2.0 |
| 5 | 12 | 0.58 | 0.50 | 2.5 | 1.6 |
| 6 | 13 | 1.61 | 1.0 | 5.5 | 3.4 |
| 7 | 32 | 8.3 | 4.4 | 0.8 | 1.0 |
| 8 | 35 | 24.5 | 11.2 | 1.2 | 1.4 |
| 9 | 3 | 1.0 | 0.5 | 2.85 | 1.5 |
| 10 | 8 | 0.68 | 0.44 | 24.0 | 5.5 |
| 11 | 10 | 0.68 | 0.50 | 4.5 | 4.0 |
| 12 | 16 | 1.30 | 0.6 | 8.8 | 4.3 |
| 13 | 25 | 44.0 | 8.5 | 4.1 | 2.8 |

The timely tPA administration (within 3 hours of symptoms) among patients with new stroke (cases 32, 35) significantly reduced unbound NR2 peptide (38-47%) and patients were independent on the modified Rankin Scale at 3 months (Table 7). In spite of an initial improvement in NIHSS scores, and a slight decrease of unbound/total NR2 peptide concentrations for case 10 after tPA (69 mg) was administered within 6 hours of admission, the patient subsequently deteriorated over the next two months (Table 7, 8). Thrombolytic therapy reduced concentrations of unbound NR2 peptide up to 90% in case 25.

Example 8

Total and Unbound NR2 Peptide Detection Assays and Performance Characteristics

Coating of the ELISA plates. Nunc MaxiSorp plate (Fisher Sci) was coated by 0.2 µg of chicken anti-NR2 IgY in 100 µL of 15 mM sodium carbonate, 35 mM sodium bicarbonate, pH 9.6. Plates were incubated overnight and then treated by 200 µL of 1 M ethanolamine, pH 8-9 for 1 hour. After rinsing in PBS buffer the plates were subsequently stored at +4° C.

Blood sample preparation. Blood (1 ml) is collected by venipuncture in sterile disposable tubes from individuals. Each one-ml blood sample should be split evenly between EDTA tubes (plasma) and clot-activator tubes (serum). For plasma, the tubes are centrifuged at 4000 g for 5 min at 4° C. For serum, the blood is allowed to clot in the tube for 20 minutes and then centrifuged at 1000 rpm for 10 minutes. The collected plasma and serum should be stored at −70° C.

Samples Pre-dilution: pipette exactly 20 µL of each serum sample into 2-3 mL volume tubes and add 980 µL of 50 mM phosphate buffer, containing 0.05% Tween 20 (PBS-T), pH 7.4 (for unbound peptide assay) or 0.1-0.5% sodium dodecylsulphate solution (or KCl) prepared on PBS-T (for total peptide assay), mix thoroughly for 10-30 min.

Direct ELISA for peptide detection. For each assay, the plate should be washed for 5 min with PBS-T. Calibrator, control, or sample (100 µL) should be then added in duplicate and incubated for 60 min at room temperature (RT). After the plate is washed three times for 15 min, 100 µL of human IgG, (6 µg/well) should be added and incubated for another 60 min at RT. After washing with buffer, Protein A-HRP is added (100 µl; 1:1,000 dilution) for 1 hour.

The reaction is revealed by tetramethylbenzedine (TMB) substrate solution after additional washing. Color reaction is developed for 5 min, stopped with acid solution (50 µl) and monitored at dual wave 450 nm/630 nm on a microplate reader. Sample buffer is also included as the blank in each assay to calculate the zero unit value. The concentration of NR2 peptide in serum is determined using the calibration curve of absorbance units of NR2 peptide versus concentration in microplate wells.

Example 9

Performance Characteristics for Unbound/Total NR2 Peptide Assays

Unbound NR2 Peptide

Operating characteristics of unbound NR2 peptide are depicted in 2×2 format in Table 9. The sensitivity and specificity of 90% and 95% at 1.0 ng/ml cutoff were calculated. Predictive values and likelihood ratios at specific cutoff points were chosen to approximate the sensitivity of 90%. At the 1.0 ng/ml cutoff value for TIA/stroke diagnosis the positive predictive value of 95% was achieved resulting in a 18-fold increase (95% CI, 10.8-25.4) in post TIA neurological complications for patients with high levels of NR2 peptide. The negative predictive value of 90% and negative likelihood ratio-of 0.05 allow misdiagnosis of TIA/stroke only in 5% of cases with stroke-like symptoms. The unbound NR2 peptide values combined with DWI/MRI data should allow 100% identification of cerebral ischemia.

TABLE 9

Unbound NR2 Peptide performance

| True Positive | 19 | 1 | False Negative |
|---|---|---|---|
| False Positive | 2 | 19 | True Negative |
| | 21 | 20 | |

Total NR2 Peptide

Operating characteristics of total NR2 peptide are presented in 2×2 format in Table 10. The lower sensitivity of 82% and about the same specificity of 96% at the 2.0 ng/ml cutoff were calculated for a total NR2 assay compared with an unbound peptide test. At the best 2.0 ng/ml cutoff value for TIA/stroke diagnosis, the positive predictive value of 93% was achieved resulting in a 20.5-fold increase in neurological complications for patients with high levels of total NR2 peptide. The negative predictive value of 88% and negative likelihood ratio of 0.18 allow misdiagnosis of TIA/stroke in 18% of cases with stroke-like symptoms. The simultaneous detection of unbound and total NR2 peptide combined with DWI/MRI data should allow 100% identification of cerebral ischemia and subdivision of cases between new and recurrent ischemic events.

TABLE 10

Total NR2 Peptide performance

| True Positive | 14 | 1 | False Negative |
|---|---|---|---|
| False Positive | 3 | 23 | True Negative |
| | 17 | 24 | |

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for diagnosing a primary ischemic neurovascular event in a patient in need thereof comprising:
    a) detecting and quantifying bound or total NR2 peptide (NR2 subunit of the N-methyl D-aspartate receptor) in a biological fluid from said patient, wherein said biological fluid is blood plasma, blood serum, or cerebrospinal fluid;
    b) detecting and quantifying unbound NR2 peptide in said biological fluid from said patient;
    c) if bound NR2 peptide is detected and quantified in step a), adding the quantity of bound NR2 peptide with the quantity of unbound NR2 quantified in step b) to arrive at a total quantity of NR2; and
    d) calculating the ratio of total:unbound NR2 peptide;
    wherein a ratio of less than 2:1 and/or a quantity of unbound NR2 peptide greater than 1.0 ng/ml is diagnostic of a primary neurovascular event.

2. A method for diagnosing a recurrent ischemic neurovascular event in a patient in need thereof comprising:
    a) detecting and quantifying bound or total NR2 peptide (NR2 subunit of the N-methyl D-aspartate receptor) in a biological fluid from said patient, wherein said biological fluid is blood plasma, blood serum, or cerebrospinal fluid;
    b) detecting and quantifying unbound NR2 peptide in said biological fluid from said patient;
    c) if bound NR2 peptide is detected and quantified in step a), adding the quantity of bound NR2 peptide with the quantity of unbound NR2 quantified in step b) to arrive at a total quantity of NR2; and
    d) calculating the ratio of total:unbound NR2 peptide; and
    wherein a ratio of greater than 2:1 and/or a quantity of total NR2 peptide greater than 2.0 ng/ml is diagnostic of a recurrent neurovascular event.

3. A method for predicting the likelihood of a recurrent ischemic neurovascular event comprising:
    a) providing a patient who has had a neurovascular event;
    b) detecting and quantifying bound or total NR2 peptide (NR2 subunit of the N-methyl D-aspartate receptor) in a biological fluid from said patient, wherein said biological fluid is blood plasma, blood serum, or cerebrospinal fluid, to arrive at a quantity of bound or total NR2 peptide;
    c) detecting and quantifying unbound NR2 peptide in said biological fluid from said patient to arrive at a quantity of unbound NR2 peptide;
    d) if bound NR2 peptide is detected and quantified in step c), adding the quantity of bound NR2 peptide with the quantity of unbound NR2 quantified in step d) to arrive at a total quantity of NR2; and
    e) calculating the ratio of total:unbound NR2 peptide;
    wherein a total:unbound NR2 peptide ratio greater than 2:1 and/or a quantity of total NR2 peptide greater than 2.0 ng/ml is diagnostic of a risk for suffering a recurrent ischemic neurovascular event.

4. The method of claim 1, wherein said biological fluid is blood plasma or blood serum.

5. The method of claim 3, wherein said biological fluid is blood plasma or blood serum.

* * * * *